US008883170B2

(12) United States Patent
Pathak et al.

(10) Patent No.: US 8,883,170 B2
(45) Date of Patent: Nov. 11, 2014

(54) ADJUVANT

(75) Inventors: Ashish Kumar Pathak, Macomb, IL (US); Vibha Pathak, Macomb, IL (US); Richard D. May, Vestavia Hills, AL (US)

(73) Assignees: Western Illinois University Research Foundation, Macomb, IL (US); Southern Research Institute, Birmingham, AL (US)

( * ) Notice: Subject to any disclaimer, the term of this patent is extended or adjusted under 35 U.S.C. 154(b) by 1437 days.

(21) Appl. No.: 12/203,272

(22) Filed: Sep. 3, 2008

(65) Prior Publication Data

US 2012/0136142 A1    May 31, 2012

(51) Int. Cl.
*A61K 39/12* (2006.01)
*C07J 17/00* (2006.01)
*C07H 15/256* (2006.01)
*A61K 39/00* (2006.01)

(52) U.S. Cl.
CPC .... *C07H 15/256* (2013.01); *A61K 2039/55577* (2013.01); *A61K 39/12* (2013.01); *C07J 17/00* (2013.01); *C12N 2760/14234* (2013.01)
USPC .................................................. 424/204.1

(58) Field of Classification Search
None
See application file for complete search history.

(56) References Cited

U.S. PATENT DOCUMENTS

| 5,817,314 | A | * | 10/1998 | So et al. | .................... | 424/184.1 |
| 6,517,842 | B1 | | 2/2003 | Hevey et al. | | |
| 2004/0242502 | A1 | | 12/2004 | Marciani | | |

OTHER PUBLICATIONS

Kensil et al (J Immunol 146:431-437, 1991).*
So et al (Mol Cells 7:178-186, 1997—Abstract only).*
Wu et al (Bioorg Med Chem Lett 17:6430-6433, 2007).*
Cmoch et al (Carbohydrate Res 343:995-1003, available online Feb. 20, 2008).*
Dana L. Swenson et al., "Monovalent Virus-like Particle Vaccine Protects Guinea Pigs and Nonhuman Primates Against Infection With Multiple Marburg Viruses" Expert Review Vaccines, vol. 7, Issue No. 4, 2008, pp. 417-429.
Dana L. Swenson et al., "Vaccine to Confer Nonhuman Primates Complete Protection Against Multistrain Ebola and Marburg Virus Infections" Clinical and Vaccine Immunology, vol. 15, Issue No. 3, Mar. 2008, pp. 460-467.
Danher Wang et al., "Complex Adenovirus-Vectored Vaccine Protects Guinea Pigs From Three Strains of Marburg Virus Challenges" Virology, vol. 353, 2006, pp. 324-332.
Charlotte Read Kensil, "Saponins As Vaccine Adjuvants." Critical Reviews in Therapeutic Drug Carrier Systems, 1996, vol. 13, Nos. 1 & 2): pp. 1-55.
Dante J. Marciani et al., "Altered Immunomodulating and Toxicological Properties of Degraded Quillaja Saponaria Molina Saponins." International Immunopharmacology, 2001, vol. 1, pp. 813-818.
Gui Liu et al., "QS-21 Structure/Function Studies: Effect of Acylation on Adjuvant Activity." Vaccine, 2002, vol. 20, pp. 2808-2815.
Hong-Soeb So et al., "Effect of a Novel Saponin Adjuvant Derived From *Quillaja saponaria* on the Immune Response to Recombinant Hepatitis B Surface Antigen." 1997, Mol. Cells, vol. 7, No. 2, pp. 178-186.

* cited by examiner

*Primary Examiner* — Craig Ricci
(74) *Attorney, Agent, or Firm* — Fitch, Even, Tabin & Flannery, LLP

(57) ABSTRACT

Methods and immunogenic compositions for generating an immune response against Marburg virus are provided. The immunogenic composition includes antigens obtained from a Marburg viral strain in combination with an oleanolic acid triterpene adjuvant.

1 Claim, No Drawings

ADJUVANT

The present invention relates to methods and compositions for generating an immune response against Marburg virus. More particularly, an immunogenic composition is provided that includes a blend of Marburg viral antigens and an adjuvant that includes oleanolic acid triterpene compounds.

BACKGROUND

The virus family filoviridae consists of two recognized viruses, Marburg virus (MBGV) and Ebola Virus (EBOV). Filoviruses are among the deadliest of acute virus infections in humans and nonhuman primates and are sufficiently contagious to cause sequential infections of persons exposed to blood and body fluids. MBGV causes severe hemorrhagic fever characterized by high mortality rates in both human and nonhuman primates. The first recognized infection of humans by a filovirus occurred in 1967 when simultaneous outbreaks of hemorrhagic fever occurred in Marburg and Frankfurt, Germany, and Belgrade, Yugoslavia. All cases were associated with laboratory workers engaged in processing kidneys from African green monkeys for cell culture production. There were 31 recognized infections and 7 deaths. Two cases of hemorrhagic fever caused by a virus similar to the 1967 MBGV were identified in Kenya in 1980. In 1987 MBGV was isolated from a fatal hemorrhagic fever case, and was subsequently shown to differ substantially from the original MBGV isolate.

Human outbreaks, though relatively few, have involved scores and sometimes hundreds of people, the viruses often infecting health care professionals and wreaking havoc on local medical infrastructures. Yet, in the context of global health statistics, filoviral disease incidence has been insufficient in the past to prompt aggressive vaccine development. After the 9/11 terrorist attack, widespread vaccination is logically assumed in case of its use as a bioterrorism agent. Moreover, these viruses have additional traits often associated historically with biological weapons, such as high infectivity in aerosol form, stability in aerosol, and even reports of active weaponization. Searches for knowledge of the scientific requirements for vaccine development were reduced to a combination of curiosity and insurance against unknowns, e.g., the possibility of viral mutation to fully contagious or even pandemic spread; or the possibility of viral emergence in new geographical areas or host species outside the currently unknown ecological niches in sub-Saharan Africa.

Several isolates of MBGV have been adapted to uniform lethality in strain 13 guinea pigs. MBGV (Musoke), MBGV (Ravn), and MBGV (Ci67) were adapted to adult strain 13 guinea pigs via serial passages of a non-guinea pig adapted virus through guinea pigs. All guinea pig adapted MBGV produce uniform lethality in both strain 13 and Hartley guinea pigs. The glycoprotein is the only membrane protein exposed on the viral surface of Marburg virus, strain Musoke, and has been isolated by expression in *E. coli* and identified by its immunoreactivity with specific antisera. GP thus appeared to be an attractive target for neutralizing antibodies. Antigenicity, and vaccine potential of MBGV GP expressed by baculovirus recombinants, was also examined. This recombinant truncated GP elicited protection against lethal challenge with the MBGV isolate from which it was constructed and less effectively against an antigenically disparate MBGV isolate; killed (irradiated) MBGV antigen was protective, in a reciprocal fashion, against MBGV types.

Previous vaccine studies have demonstrated that whole, irradiated MBGV, when used to vaccinate guinea pigs in the presence of the RIBI adjuvant, results in complete protection from disease and death. In turn, the glycoprotein (GP) antigen has emerged as an important and perhaps necessary component of efficacious vaccines. Both antibodies and T cells appear to have roles in filovirus immunity, but significant gaps remain in the understanding and measurement of vaccine-induced immune responses that prevent or mitigate filovirus disease.

Immune stimulants play an important and essential role in development of vaccine adjuvants and drug delivery systems. Subunit vaccines are designed to include only the antigens required for protective immunization and to be safer than whole-inactivated or live-attenuated vaccines. However, the purity of the subunit antigens and absence of immunomodulatory components often result in weaker immunogenicity.

Adjuvants are a heterogeneous group of compounds that are capable of triggering or enhancing an immune response against an otherwise poorly immunogenic entity and can be broadly separated into two classes based on their principal mechanisms of action; (a) vaccine delivery system and (b) immunostimulatory adjuvants. Vaccine delivery systems are generally particulate (e.g., emulsions, microparticles, ISCOMs and liposomes), and mainly function to improve the uptake of antigens by the immune system, and stimulate antigen-presenting cells (APC) to assist in mounting an immune response. Immunostimulatory adjuvants are predominantly derived from pathogens and often pathogen associated molecular patterns (PAMP), which activate cells of the innate system and then focus the acquired immune response. In some studies, delivery systems and immunostimulating agents have been combined.

There are several features that are necessary for an adjuvant to be effective: (a) it should be non-toxic or at least have a wide therapeutic range (effective dose<<toxic dose); (b) it should form a depot at the injection site, (c) it should increase antigen (or antigen-adjuvant complex) uptake into APCs; (d) it should mobilize APCs so that they travel to the draining lymph nodes; (e) it should up-regulate the necessary additional signals on APCs to prime T-cells (CD4+ and CD8+) efficiently, (f) ideally, different adjuvants would lead to either a preferential humoral (antibody, Th2-like) or cell mediated (CTL, Th1-like) immune response. Several synthetic and other defined adjuvants are used or are currently being tested and evaluated. These include; alum, poloxamers, MF59, lipopeptides, the synthetic peptide analog PAM3Cys, muramyl dipeptides and derivatives, CpG oligonucleotides, polycationic peptides, carbohydrate polymer derivatives of mannan, chitosan, 1,3-β-glucans, etc. and saponins.

Alum is not capable of generating cytolytic T-lymphocytes (CTL) that are prerequisite for the clearance of intracellular pathogens. This inability to generate CTL is due to the manner in which the immune system responds but produces >90% Th2 response.

Saponin-based adjuvants such as Quil-A, QS-21 and GPI-0100 have been applied to a variety of vaccine formulations because of the ability to promote CTL and Th1 responses. Saponins are a heterogeneous group of sterol glycosides or triterpenoid glycosides that are present in a wide range of plant species. Specially, triterpene saponins have been identified with strong immunoenhancing capacity and toxicity, but they cause strong local reactions at the site of injection mainly due to their lytic properties. In particular, the saponins from *Quillaja saponaria* Molina, *Gypsophila* sp. and *Saponaria officinalis* have unique immunostimulating and immunomodulating properties. An enriched heterogeneous mixture of saponins named Quil-A was extracted from the *Quillaja* bark that possessed adjuvant properties. The toxicity profile of Quil-A precludes expanded use in human vaccines but is being used commercially in a veterinary vaccine. The four most predominant saponins (QS-7, QS-17, QS-18 & QS-21) and about 23 other minor saponin contents from *Quillaja saponaria* extracts were purified to near homogeneity by reversed-phase HPLC.

The characteristic feature of these saponins is the presence of an aldehyde group at C-4 of the aglycones (quillaic acid and gypsogenic acid). Generally, these saponins are bidesmosides with branched sugar substitution at C-3 and C-28. The presence of a 3,5-dihydroxy-6 methyloctanoic acid ester on C-28 fucose residue is unique to *Quillaja* saponins and plays a critical role in producing cytotoxic T-lymphocyte (CTL) responses. Among all *Quillaja* saponins, single isolated and purified QS-21 has been shown to have the most potent adjuvant activity, as a complex amphipathic molecule that readily forms micelles. QS-21 is potent for CTL induction, inducing Th1 cytokines (IL-2, IFN-γ) and antibodies of the IgG2a isotype and is undergoing several clinical trials as an adjuvant for cancer vaccines (melanoma, breast and prostate), and infectious diseases (HIV-1, influenza, herpes, malaria, hepatitis B). Doses of 200 µg or higher of QS-21 in humans have been associated with significant local reactions, but lower doses appear to be well tolerated. The other main drawback of QS-21 is pH dependent stability. Due to acylated octanoic side chain, the stability is a problem leading to deacylation resulting in loss of overall adjuvant activity and degradation on storage at ambient temperature.

The purification and characterization of adjuvant active saponins from *Quillaja saponaria* has also enabled a correlation between structure and function. The removal of the fatty acid domain to deacylated saponins resulted in the loss of production of antibody and CTL-stimulating capacity. Similarly, reduction of the C-4 aldehyde or blocking it with amine caused this same loss of activity. This clearly suggests that this functional group is critical for the adjuvant's activity, probably by interacting with free amino groups on the surface on a lymphocyte or APC. Also, the aldehyde may stabilize a saponin-antigen complex through imine formation. All the saponins contain a single glucuronic acid that may impart an overall anionic charge to the saponins at physiological pH, as the conversion of acid groups to amides does not affect overall adjuvant activity. In general, for strong adjuvant activity of oleanolic acid-containing saponins, three factors are critical to stimulate antibody and CTL production: a) presence of an aldehyde group, b) presence of a fatty acid chain, and c) sugars (for receptor activity and micelle formation).

SUMMARY

A method is provided for generating an immune response in a subject against Marburg virus. The method includes administering to a subject an immunogenic composition comprising antigens obtained from a Marburg viral strain. The antigens obtained from a Marburg viral strain are administered to the subject in combination with an adjuvant in a pharmaceutical carrier. The adjuvant includes a compound having a structure wherein $R_1$ is H or an oligosaccharide with from about 1 to about 12 saccharide units, in another aspect about 1 to about 8 saccharide units, $R_2$ is $NH(CH_2)_xCH_3$, where x is about 3 to about 23, in another aspect x is about 3 to about 15, and $R_3$ is H or OH. Administering a subject a combination of antigens obtained from a Marburg viral strain and adjuvant in a pharmaceutical carrier is effective for generating an immune response in the subject.

In an important aspect, $R_1$ includes from about 1 to about 8 saccharide units. Oligosaccharides which may be utilized include the structure wherein $R_4$ is H and y is 1 to 8, in an important aspect y is 1 to 6.

The immunogenic composition may be administered to a subject by a number of different routes. Administrative routes that may be utilized include intramuscular administration, intranasal administration, oral administration, transdermal administration, and transmucosal administration. The antigens obtained from the Marburg vial strain may include glycoproteins.

Immunogenic compositions are prepared by a method that includes preparing antigens from a Marburg viral strain and blending the antigens with an adjuvant having the above-identified formula.

DETAILED DESCRIPTION

The above and other problems addressed above are solved by the preferred embodiments discussed below. The following description is of the best mode presently contemplated for practicing the invention. This description is not to be taken in a limiting sense, but is made merely for the purpose of describing the general principles of the invention.

A vaccine formulation is provided for Marburg virus along with a method for making a vaccine for Marburg virus. The vaccine formulation is effective for generating an immune response in a subject. The vaccine formulation includes an oleanolic acid triterpene adjuvant.

Marburg Viral Antigens

Marburg viral antigens may be produced using a number of techniques which are known in the art. For example, U.S. Pat. No. 6,517,842, which is incorporated herein by reference, describes the use of DNA fragments that encode a protective antigen from the Marburg virus. Swenson et al., Expert Review of Vaccines, Vol. 7, No. 4, pages 417-429 (2008), which is incorporated herein by reference, describes expression of glycoprotein and VP40 matrix protein from Marburg virus. Swenson et al., Clinical and Vaccine Immunology, Vol. 15, No. 3, pages 460-467 (2008), which is incorporated herein by reference, describes expression of multiple antigens from five different filoviruses de novo. Further, Wang et al., Virology, Vol. 353, No. 2, pages 324-332 (2006), which is incorporated by herein by reference, describes expression of glycoprotein fusion proteins.

Oleanolic Acid Triterpene Adjuvants

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate Th1 or Th2 cell-specific immune responses; and
(8) ability to selectively increase appropriate antibody isotype levels (for example, IgA or IgG1) against antigens.

Provided herewith are oleanolic acid triterpene based adjuvants that have a low toxicicity. In this aspect, the adjuvant compositions have a toxicity of about 4 mg/kg body weight or more.

Adjuvant stability plays a critical role in the formulation of vaccines. QS-21 that is esterified at the 4-OH group of fucose undergoes facile intramolecular transeterification to form mixtures of 3- and 4-esters depending on pH. This facile migratory aptitude of the ester accounts form its ease of hydrolysis and the instability of QS-21 in vaccine preparations stored at physiological pH. Elimination of the toxic octanoic ester side chain of QS-21 results in a deacyl saponin (hydrolyzed saponin). Amidation of the glucuronic acid group with an aliphatic chain (preferably dodecyl) results in the GPI-0100 adjuvant compound. These types of oleanolic acid triterpene based adjuvants are easy to manufacture and have a storage stability of about 1 month at room temperature (25° C.) and 6 months or greater at a storage temperature of about 0° C.

Immunogenic compositions which include oleanolic acid triterpene adjuvants with Marburg viral antigens are effective for enhancing an immune response over the use of immunogenic compositions that do not include oleanolic acid triterpene compounds. In this aspect, oleanoic acid triterpene adjuvants are able to enhance IgG1 response by at least about 42% over the IgG1 response seen without the use of oleanolic acid triterpenes. Further, immunogenic compositions including oleanolic acid triterpene adjuvants enhance antigen specific T cell response by at least about 34% over the response seen without the use of oleanolic acid triterpenes.

Vaccine Preparation and Use

Vaccines are prepared by combining Marburg viral antigens with adjuvant. The concentration of antigen in an immunogenic composition according to the invention is in general 1 to 95 weight percent, based on the total weight of the immunogenic composition.

The immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

Immunogenic compositions may take the form of solutions, suspensions, tablets, pills, capsules, sustained release formulations or powders and contain 1 to 95% of the immunogenic compositions of the present invention.

The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated immune response. Precise amounts of antigen and immunogenic composition to be administered depend on the judgment of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

EXAMPLES

A better understanding of the present embodiment and of its many advantages may be clarified with the following example, given by way of illustration.

Example 1

Adjuvant Synthesis

The generic structure for saponin(s) is derived on the basis of structure-activity profiles of saponins Quil-A, QS-7, QS-17, QS-18, QS-21 and GPI-0100. The proposed saponins possess a hydrophobic chain (C8-C14) attached at the C-28 carboxyl group through an amide linkage (for CTL production and stability), a free aldehyde group (for co-stimulatory effect) at C-4, and oligosaccharide [mannopyranose units (6 to 9)] at C-3 (for receptor interaction and formation of micelles) to achieve potent adjuvant activity.

The chemical synthesis of the saponins was achieved from the genin [gypsogenin] using similar procedures for other known synthetic saponins of diosgenin and oleanolic acid. Several efficient syntheses of mannan polysaccharides have also been reported that can be used, i.e., di- to hexasaccharide 1,2-linked α-mannopyran oligomers, octameric (1→2) linked mannan and hexameric branched mannans, comb-like mannohexose trimer having disaccharide as repeating unit, hexa- and nona-saccharides as di- and trimer of the trisaccharide units of mannans etc. Initially towards the synthesis of saponin adjuvants, a *Gypsophilla* sp. saponin mixture (from Sigma) was used. Gypsogenin is the only aglycone found in all the saponins isolated so far from *Gypsophilla* sp.

Gypsogenin was isolated in large scale by the cleavage of the sugar residues in saponins by acid hydrolysis using 2N $H_2SO_4$ in water-ethanol (1:1) as reported in the literature. In brief, after acid hydrolysis and upon cooling, the crude genin was collected by filtration and gypsogenin was purified by column chromatography as represented below:

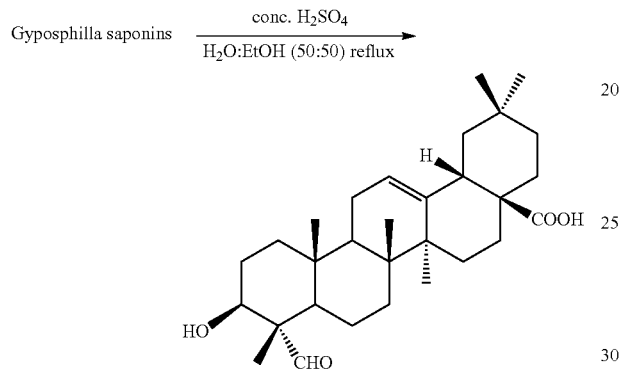

100 gm of commercially available gypsophilla saponin (Sigma, Cat# S-1252, Lot#117C-0138) was dissolved in water-ethyl alcohol (400 ml, 1:1 v/v). To the stirring solution of saponin was added 11.2 ml of conc. Sulfuric acid dropwise and reaction mixture was stirred overnight under reflux. The solid thus obtained was filtered through Whatman glass microfibre filters (GF/D). It was resuspended in water-ethyl alcohol (400 ml, 2:1 v/v) and added 11.2 ml of conc. sulfuric acid dropwise. The reaction mixture was refluxed again for 24 hours followed by filtration through Whatman glass microfibre filters (GF/D). The sticky dark brown solid was extracted under reflux with 1.0 liter of chloroform in a Soxhlet apparatus. The dark brown chloroform solution was passed through anhydrous sodium sulfate and concentrated under vacuum to a dark brown solid. This solid was dissolved in 100 ml of chloroform in a 500 ml round bottom flask. To it was added 100 g of silica gel 60 (230-400 Mesh) and concentrated to dryness under vacuum to produce slurry. The slurry was loaded on a silica gel 60 packed column and was chromatographed using Cyclohexane-Ethyl acetate (2:1) as mobile phase to produce pure gypsogenin (6.5 gm) as colorless solid (m.p. 235° C. decomposed). The pure gypsogenin was kept in cold (below −4° C.) until further use as decomposition was seen at room temperature storage by Silica gel G TLC [mobile phase: Cyclohexane-Ethyl acetate (2:1), visualization after spraying with 10% $H_2SO_4$ in water solution and heating at 120° C.]. The purity of gypsogenin was checked periodically on the stored sample and no change was observed even after 1 year.

Example 2

Amide Derivative of Gypsogenin

The synthesis of dodecylamide derivative of gypsogenin is represented below:

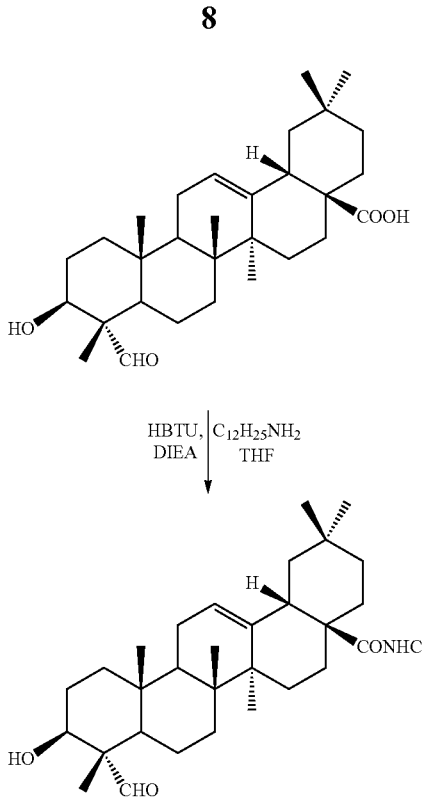

Gypsogenin (1.30 g, 2.76 mmol) was dissolved in dry THF (40 mL) under argon atmosphere at room temperature. DIEA (1.5 ML, 8.28 mmol) and HBTU (1.30 g, 3.31 mmol) were added to the above solution and reaction mixture was stirred for 1 hr at room temperature to produce an intermediate complex. Dodecylamine (614 mg, 3.31 mmol) was added to the reaction mixture which was further stirred for 48 hours at room temperature. TLC using cyclohexane-ethylacetate (1:1) as mobile phase showed the completion of reaction. The reaction was diluted with chloroform, washed with water, dried over sodium sulfate and concentrated to a solid. Column chromatographic purification of crude product on silica gel G using cyclohexane-ethylacetate (3:1 to 2:1) as mobile phase gave pure dodecylamide derivative of gypsogenin in 65% yield. m.p. 85-87° C.

Example 3

Synthesis of α(1→6)-linked Octamannan (12)

Synthesis of octamannan is described in the sequence of reaction as represented in the scheme below. Synthesis of glycosides 3, 4, 5 and 6 are similar to the reported in literature (Pathak et al. *Org. Lett.*, 10, 145, 2008). Synthetic details of other glycosides are as following.

Disaccharide 7: To the solution of 6 (5.00 g, 5.38 mmol) in 100 ml dry $CH_2Cl_2$ was added DAST (0.99 mL, 8.07 mmol) at 0° C. followed by NBS (1.44 g, 8.07 mmol). The reaction mixture was stirred overnight during which time it was allowed to rise to room temperature. TLC indicated the total consumption of the starting material and the formation of one new compound. The solvent was removed under vacuum, and the resulting residue was dissolved in chloroform. The solution was washed with saturated aqueous $NaHCO_3$. The organic layer was dried over $Na_2SO_4$ and concentrated. The residue was purified by silica gel 60 column chromatography using mobile phase Cyclohexane-Ethyl acetate (3:1) to furnish 0.68 g of 7 (4.14 g, 91% yield) as a white foam. m.p. 90-93° C.

Disaccharide 8: To the solution of disaccharide 6 (4.00 g, 3.59 mmol) in dry CH$_2$Cl$_2$ (50 ml) and dry MeOH (50 ml) was added acetyl chloride (0.75 ml). The reaction mixture was stirred for 36 hrs at room temperature. TLC indicated the total consumption of the starting material and the formation of one new compound. The solvent was removed under vacuum, and the resulting residue was purified by disaccharide (3.82 g, quantitative yield) as a white foam. m.p. 85-88° C.

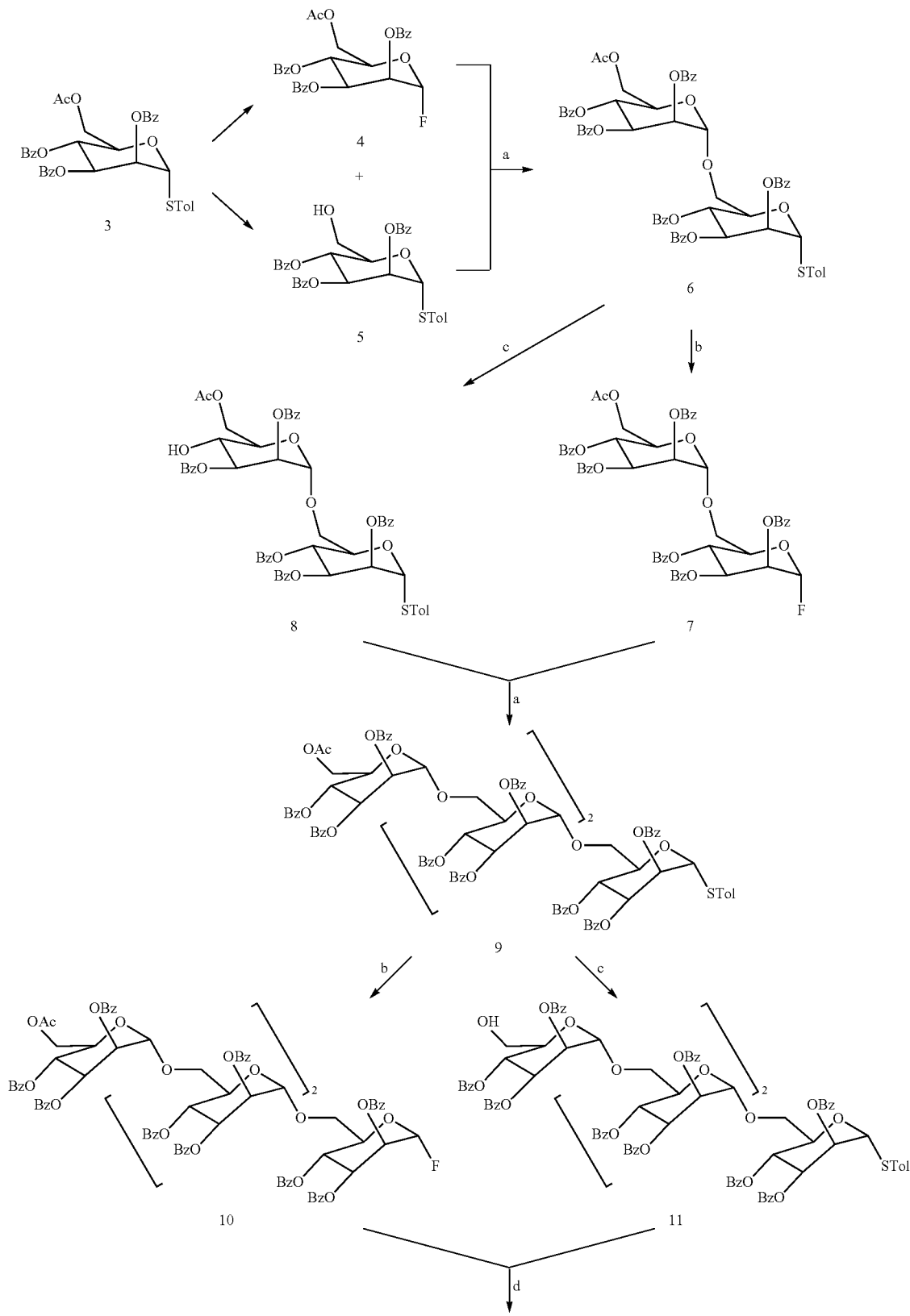

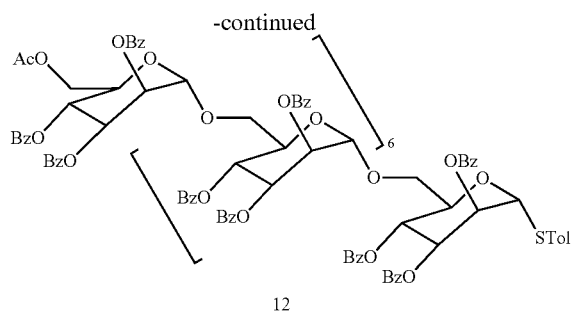

Glycosylation Reactions. Reactions and Reagents. (a) AgClO$_4$, SnCl$_2$, dry CH$_2$Cl$_2$, 4 A Mol sieves, rt, overnight, 6: 97%, 9: 80%. (b) DAST, NBS, dry CH$_2$Cl$_2$, −20° C., 4 h, 7: 91%, 10: 84%; (c) AcCl/MeOH/CH$_2$Cl$_2$ (1:20:20 v/v), rt, overnight, 8: quantitative yield, 11: 86%, (d) Cp$_2$HfCl$_2$, AgOTf, dry CH$_2$Cl$_2$, 4 A Mol sieves, rt, overnight, 12: 61%.

Tetrasaccharide 9: To a stirred suspension of freshly activated 4 A molecular sieves (3.0 g) in 20 ml dry CH$_2$Cl$_2$ was added AgClO$_4$ (1.23 g, 5.92 mmol) and SnCl$_2$ (1.12 g, 5.92 mmol). The mixture was cooled to 0° C. before a solution of 7 (3.20 g, 2.96 mmol), 8 (3.82 g, 3.56 mmol) and 2,6-lutidine (0.61 mL, 2.96 mmol) in dry CH$_2$Cl$_2$ (10 ml) was added through a cannula. The reaction mixture was stirred overnight during which time it was allowed to rise to room temperature. TLC indicated the formation of one new major compound. The mixture was filtrated through a Celite pad, the solvent was removed under vacuum, and the resulting residue was dissolved in chloroform. The solution was washed with saturated aqueous NaHCO$_3$ solution. The organic layer was dried over Na$_2$SO$_4$ and concentrated. The residue was purified by silica gel 60 column chromatography using mobile phase Cyclohexane-Ethyl acetate (2:1) to furnish 9 (5.20 g, 80% yield) as a white foam. m.p. 137-140° C.

Tetrasaccharide 10: To the solution of 9 (1.50 g, 0.73 mmol) in 20 ml dry CH$_2$Cl$_2$ was added DAST (0.13 ml, 1.09 mmol) at 0° C. followed by NBS (194 mg, 1.09 mmol). The reaction mixture was stirred overnight during which time it was allowed to rise to room temperature. TLC indicated the total consumption of the starting material and the formation of one new compound. The solvent was removed under vacuum, and the resulting residue was dissolved in chloroform. The solution was washed with saturated aqueous NaHCO$_3$. The organic layer was dried over Na$_2$SO$_4$ and concentrated. The residue was purified by silica gel 60 column chromatography using mobile phase Cyclohexane-Ethyl acetate (2.5:1) to furnish 10 (1.20 g, 84% yield) as a white foam. m.p. 137-140° C.

Tetrasaccharide 11: To the solution of disaccharide 9 (1.50 g, 0.73 mmol) in dry CH$_2$Cl$_2$ (20 ml) and dry MeOH (20 ml) was added acetyl chloride (0.28 ml). The reaction mixture was stirred for 36 hrs at room temperature. TLC indicated the total consumption of the starting material and the formation of one new compound. The solvent was removed under vacuum, and the resulting residue was purified by silica gel 60 column chromatography using mobile phase Cyclohexane-Ethyl acetate (2:1) to furnish pure disaccharide (1.27 g, 86% yield) as a white foam. m.p. 142-145° C.

Octasaccharide 12: A solution of 10 (378 mg, 0.15 mmol), 11 (300 mg, 0.15 mmol) and freshly activated 4 A molecular sieves (250 mg) in dry CH$_2$Cl$_2$ (15 mL) was cooled to 0° C. To it was added Cp$_2$HfCl$_2$ (6 mg, 0.02 mmol) followed by AgOTf (9.7 mg, 0.04 mmol). The reaction mixture was stirred overnight during which time it was allowed to rise to room temperature. TLC indicated the formation of one new major compound. The mixture was filtrated through a Celite pad, the solvent was removed under vacuum, and the resulting residue was dissolved in chloroform. The solution was washed with saturated aqueous NaHCO$_3$ solution. The organic layer was dried over Na$_2$SO$_4$ and concentrated. The residue was purified by silica gel 60 column chromatography using mobile phase Cyclohexane-Ethyl acetate (1.5:1) to furnish 12 (358 mg, 61% yield) as a white foam. m.p. 138-141° C.

Example 4

Synthesis of Saponins

Saponin A.

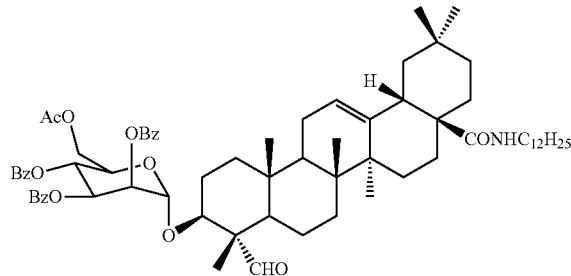

To a stirred solution of gypsogenin dodecyl amide (2) (250 mg, 0.39 mmol) and glycoside 3 (211 mg, 0.33 mmol) in 10 ml dry CH$_2$Cl$_2$ was added 80 mg freshly activated 4 A molecular sieves. The suspension was cooled to 0° C. and NIS (88 mg, 0.39 mmol) was added, followed by triflic acid (15 µg, 0.17 mmol). The reaction mixture was stirred at 0° C. for 30 mins. TLC indicated the total consumption of the starting material and the formation of one new major compound. The mixture was filtrated through a Celite pad, the filtrate was diluted with chloroform, washed with aqueous saturated NaHCO$_3$, saturated sodium thiosulfate and deionized water. The organic layer was dried over Na$_2$SO$_4$ and concentrated. The residue was purified by silica gel 60 column chromatography (3:1 hexanes:EtOAc) to furnish Saponin A as a colorless solid (313 mg, 70% yield).

Saponin B (Also Known as Saponin 1):

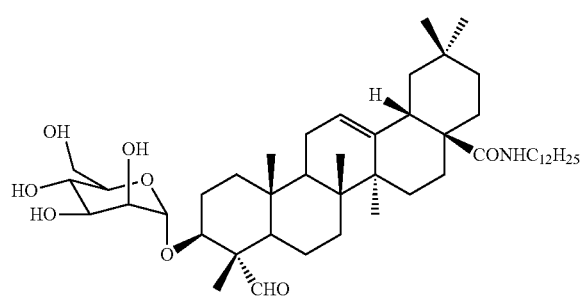

Saponin A (120 mg, 0.69 mmol) was dissolved in dry MeOH (2 ml) and to solution was added 7N $NH_3$/MeOH (5 ml). The reaction was stirred overnight at room temperature and TLC($CHCl_3$-MeOH 7:1) showed completion of the reaction. The mixture was concentrated to syrup that was purified over silica gel 60 using $CHCl_3$-MeOH (7:1) as mobile phase to afford Saponin B (Saponin 1) as colorless solid. The solid was dissolved in 5 mL of deionized water, filtered through 0.5 micron filter and lyophilized to solid (57 mg, 67%). Saponin C.

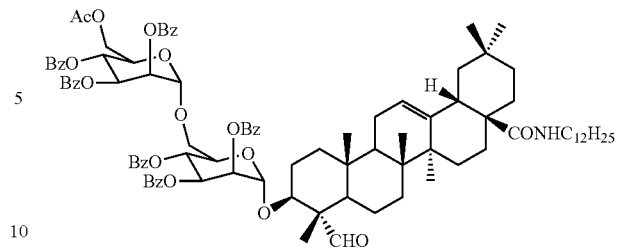

To a stirred solution of gypsogenin dodecly amide (150 mg, 0.24 mmol) and glycoside 6 (150 mg, 0.14 mmol) in 2 mL dry $CH_2Cl_2$ was added 80 mg freshly activated 4 A molecular sieves. The suspension was cooled to 0° C. and NIS (50 mg, 0.25 mmol) was added, followed by triflic acid (3 µL, 0.3 mmol). The reaction mixture was stirred at 0° C. for 30 mins. TLC indicated the total consumption of the starting material and the formation of one new major compound. The mixture was filtrated through a Celite pad, the filtrate was diluted with chloroform, washed the aqueous saturated $NaHCO_3$, saturated sodium thiosulfate and deionized water. The organic layer was dried over $MgSO_4$ and concentrated. The residue was purified by silica gel column chromatography (5:1 hexanes:EtOAc) to furnish Saponin C as a colorless solid (150 mg, 66% yield).

Saponin D.

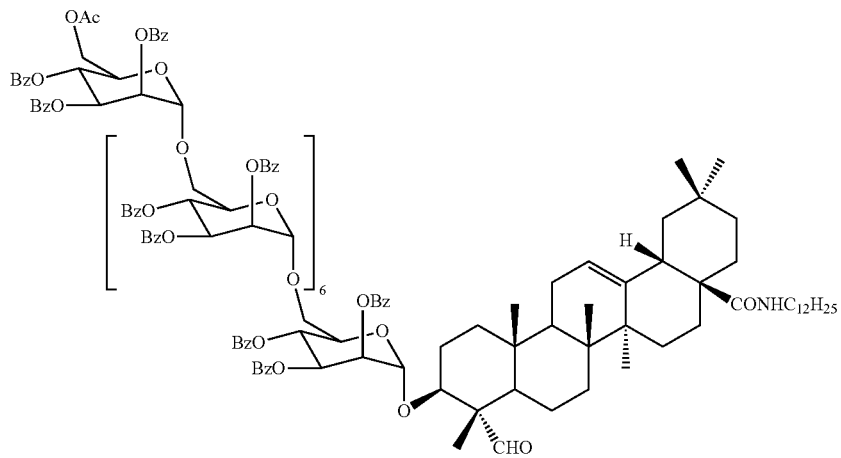

To a stirred solution of gypsogenin dodecly amide (2) (188 mg, 0.29 mmol) and glycoside 12 (650 mg, 0.16 mmol) in 25 ml dry $CH_2Cl_2$ was added 150 mg freshly activated 4 A molecular sieves. The suspension was cooled to 0° C. and NIS (66 mg, 0.29 mmol) was added, followed by triflic acid (0.08 ml, 0.02 mmol). The reaction mixture was stirred at 0° C. for 3 hrs. TLC indicated the total consumption of the starting material and the formation of one new major compound. The mixture was filtrated through a Celite pad, the filtrate was diluted with chloroform, washed the aqueous saturated $NaHCO_3$, saturated sodium thiosulfate and deionized water. The organic layer was dried over $Na_2SO_4$ and concentrated. The residue was purified by silica gel column chromatography (2:1 hexanes:EtOAc) to furnish Saponin D as a colorless solid (580 mg, 79% yield). m.p. 172-174° C.

Saponin E (Code: WIUVP1-42).

Saponin D (530 mg, 0.12 mmol) was dissolved in a 3:2 mixture of dry MeOH/CH$_2$Cl$_2$ (15 ml) and to solution was added 7N NH$_3$/MeOH (10 ml). The reaction mixture was stirred overnight at room temperature and TLC(CHCl$_3$-MeOH—H$_2$O, 65:35:10, organic layer) showed completion of the reaction. The mixture was concentrated to syrup that was purified over silica gel 60 using CHCl$_3$-MeOH—H$_2$O (65:35:10, organic layer) as mobile phase to afford Saponin E as colorless solid. The solid was dissolved in 5 ml of deionized water, filtered through 0.5 micron filter. It was dialyzed against deionized water using dialysis tubing (3500 MWCO) to remove any organic impurities, followed by lyophilization to a solid (198 mg, 83%). m.p. 227-230° C.

Gypsogenin, dodecyl genin, saponin 1, and Quil A were tested for their acute toxicity and ability to influence the immune response to influenza hemagglutinin antigen in BALB/c mice. WIUVP1-42 and WIUVP1-55 were tested for their ability to influence the immune response to inactivated Marburg virus in BALB/c mice.

Example 5

Acute Toxicity Study of Gypsogenin (1), Dodecyl Genin (2), Saponin 1, and Quil A Each group of mice contained five males and five females, all approximately 20 gm in body weight. Animals were given a single subcutaneous (s.c.) injection of various amounts of the compounds (formulated in DMSO), ranging from 50 µg to 4 mg and observed for morbidity and mortality for the following week.
The survival results were as follows:

| Group | Compound | Dose | 7-Day Survival | |
|---|---|---|---|---|
| | | | Males | Females |
| 1 | Gypsogenin | 4 mg | 100% | 100% |
| 2 | " | 2 mg | 100% | 100% |
| 3 | " | 1 mg | 100% | 100% |
| 4 | " | 500 µg | 100% | 100% |
| 5 | " | 250 µg | 100% | 100% |
| 6 | Dodecyl genin | 4 mg | 100% | 100% |
| 7 | " | 2 mg | 100% | 100% |
| 8 | " | 1 mg | 100% | 100% |
| 9 | " | 500 µg | 100% | 100% |
| 10 | " | 250 µg | 100% | 100% |
| 11 | Saponin 1 | 4 mg | 100% | 80% |
| 12 | " | 2 mg | 100% | 80% |
| 13 | " | 1 mg | 100% | 100% |
| 14 | " | 500 µg | 100% | 100% |
| 15 | " | 250 µg | 100% | 100% |
| 16 | Quil A | 400 µg | 0% | 0% |
| 17 | " | 200 µg | 0% | 0% |
| 18 | " | 100 µg | 0% | 0% |
| 19 | " | 50 µg | 80% | 100% |

Thus, the maximum tolerated dose (MTD) for gypsogenin and dodecyl genin was above 4 mg and therefore not reached in this study. The MTD for saponin 1 was >4 mg for males and 1 mg for females. The MTD for Quil A was <50 µg for males and 50 µg for females. Animals treated with gypsogenin, dodecyl genin, and Sap 1 experienced lethargy, hair loss, and skin irritation at the injection site.

This study demonstrates the general lack of toxicity for the three compounds, gypsogenin, dodecyl genin, and saponin 1.

Example 6

Immunogenicity Study of Gypsogenin, Dodecyl Genin, Saponin 1, and Quil A

In order to test whether these compounds exhibited any adjuvanticity, they were combined with the recombinant hemagglutinin antigen (rHA) of influenza A and immunized mice. Each group contained five BALB/c mice. Animals were immunized s.c. on Days 1 and 22 with the mixtures shown in the study design below. On Day 43, animals were bled for serum preparation and spleens were removed for to assess lymphoproliferation upon vitro boosting.

| Group Assignments | | |
|---|---|---|
| Group | Antigen | Compound |
| 1 | None (PBS) | None (PBS) |
| 2 | rHA (5 μg) | " |
| 3 | " | Quil A (10 μg) |
| 4 | " | Gypsogenin (100 μg) |
| 5 | " | Dodecyl genin (100 μg) |
| 6 | " | Saponin 1 (100 μg) |

Antibody (Ab) titers were determined by a sandwich ELISA in which plates were coated with HA. Serum dilutions were placed in the wells in duplicate. The HRP-conjugated secondary antibodies were specific for total IgG or the IgG1, IgG2a, or IgG2b isotypes. The reciprocal of dilution giving an OD reading at 0.5 was considered the titer. Results are shown below.

| Group Anti-rHA Titers | | | | |
|---|---|---|---|---|
| Group | Total IgG | IgG1 | IgG2a | IgG2b |
| 1 | 123 | 6 | 5 | 14 |
| 2 | 9104 | 2088 | 8069 | 257 |
| 3 | 47,000 | 13,283 | 30,575 | 3950 |
| 4 | 1136 | 3220 | 348 | 1118 |
| 5 | 3418 | 20,984 | 6600 | 1466 |
| 6 | 5130 | 29,100 | 446 | 2008 |

Antigen-specific proliferation was tested by restimulating spleen cells with medium (background), concanavalin A (Con A; a T cell mitogen that should stimulate all T cells), and rHA for 4 days and measuring tritiated thymidine ($^3$H-TdR) incorporation. The results are shown in the following table:

| Lymphoproliferation | | | |
|---|---|---|---|
| Group | Medium | Con A | rHA |
| 1 | 692 | 262,967 | 1354 |
| 2 | 903 | 293,294 | 4813 |
| 3 | 438 | 263,829 | 2966 |
| 4 | 356 | 321,750 | 8507 |
| 5 | 772 | 278,393 | 30,402 |
| 6 | 268 | 232,769 | 3696 |

Example 7

Immunogenicity Study of WIUVP1-42 and WIUVP1-55

Using inactivated Marburg virus (MBGV) as the test antigen, WIUVP1-55 (GPI-0100) and WIUVP1-42 were tested for their ability to influence the immune response in BALB/c mice. After s.c. immunization on Days 1, 15, and 29, anti-MBGV Ab generation (total IgG, IgG1, IgG2a by ELISA) was determined.

| Group Assignments | | |
|---|---|---|
| Group | Antigen (dose/mouse) | Compound |
| 1 | None (PBS) | PBS only (no MBGV) |
| 2 | MBGV (25 μg) | PBS (MBGV only) |
| 3 | " | WIUVP1-55 (100 μg) |
| 4 | " | WIUVP1-42 (250 μg) |
| 5 | " | WIUVP1-42 (100 μg) |
| 6 | " | WIUVP1-42 (50 μg) |
| 7 | " | WIUVP1-42 (25 μg) |

Ab titers were determined by a sandwich ELISA in which plates was coated with MBGV. Serum dilutions were placed in the wells in duplicate. The HRP-conjugated secondary antibodies were specific for total IgG or the IgG1 or IgG2a isotypes. The reciprocal of dilution giving an OD reading at 0.5 was considered the titer. The results are shown below.

| Group Anti-MBGV Titers | | | |
|---|---|---|---|
| Group | Total IgG | IgG1 | IgG2a |
| 1 | <10 | <10 | <10 |
| 2 | 20,300 | 68,600 | 71 |
| 3 | 37,100 | 102,400 | 280 |
| 4 | 40,400 | 97,600 | 400 |
| 5 | 26,300 | 87,500 | <100 |
| 6 | 38,600 | 82,100 | <100 |
| 7 | 25,200 | 72,100 | 146 |

What is claimed is:

1. An adjuvant having a structure

[Chemical structure showing a pentacyclic triterpene with substituents $R_1O$, CHO, $COR_2$, $R_3$, and H]

wherein R1 is an oligosaccharide having a structure selected from the group consisting of

[Chemical structures of oligosaccharides with $R_4O$ substituents], or

-continued
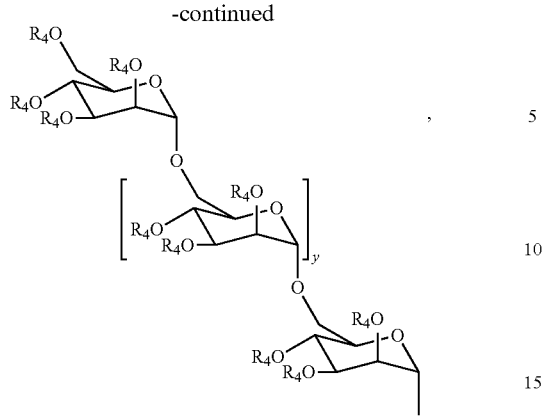
wherein $R_4$ is H and y is 1 to 6, $R_2$ is $NH(CH_2)xCH_3$, wherein x is about 3 to about 23, and $R_3$ is H or OH.
* * * * *